(12) United States Patent
Livingstone

(10) Patent No.: US 6,927,367 B2
(45) Date of Patent: Aug. 9, 2005

(54) AUTOMATIC TEMPERATURE CONTROL SYSTEM AND METHOD

(75) Inventor: David Edward Livingstone, Harrietsville (CA)

(73) Assignee: Kernohan, David Ian, St. Thomas (CA); Partial Interest ( * ) Notice: Subject to any disclaimer, the term of this patent is extended or adjusted under 35 U.S.C. 154(b) by 25 days.

(21) Appl. No.: 10/677,667

(22) Filed: Oct. 3, 2003

(65) Prior Publication Data

US 2005/0072772 A1 Apr. 7, 2005

(51) Int. Cl.⁷ ............................................. H05B 1/02
(52) U.S. Cl. ....................... 219/490; 219/204; 219/494
(58) Field of Search ................... 219/482–494, 219/507–510, 200–202, 204, 211, 217, 535, 538, 542, 544

(56) References Cited

U.S. PATENT DOCUMENTS

| | | | |
|---|---|---|---|
| 744,739 A | * 11/1903 | fLiess | ................ 219/201 |
| 2,662,961 A | 12/1953 | Sargent | |
| 3,667,315 A | * 6/1972 | Polly, Sr. | ................ 219/204 |
| 3,733,463 A | 5/1973 | Low et al. | |
| 3,982,163 A | 9/1976 | Hill | |
| 4,219,724 A | 8/1980 | Allvin | |
| 4,243,875 A | 1/1981 | Chang | |
| 4,288,271 A | 9/1981 | Campbell, Jr. et al. | |
| 5,072,093 A | 12/1991 | Scheuerer | |
| 5,175,953 A | * 1/1993 | Lesnock | ................ 43/24 |
| 5,294,775 A | 3/1994 | Carrier | |
| 5,352,862 A | 10/1994 | Barr | |
| 5,605,643 A | 2/1997 | Reece | |
| 5,757,165 A | 5/1998 | Minks | |
| 6,093,908 A | 7/2000 | Haag | |
| 6,107,783 A | 8/2000 | Minks | |
| 6,124,577 A | 9/2000 | Fristedt | |
| 6,172,342 B1 | 1/2001 | Khafagy et al. | |
| 6,237,675 B1 | 5/2001 | Oehring et al. | |
| 6,268,588 B1 | 7/2001 | Hazebrouck et al. | |
| 6,414,270 B1 | 7/2002 | Sugiyama et al. | |
| 6,495,799 B1 | 12/2002 | Pillsbury, IV et al. | |
| 2003/0006228 A1 | 1/2003 | Nagatomo | |
| 2003/0024924 A1 | 2/2003 | Fristedt | |
| 2003/0111453 A1 | 6/2003 | Haag et al. | |
| 2004/0007567 A1 | 1/2004 | Downey et al. | |

* cited by examiner

*Primary Examiner*—Tu Hoang
(74) *Attorney, Agent, or Firm*—Anissimoff & Associates

(57) ABSTRACT

A system and method are provided for automatically warming a grip surface, such as handlebars, of a vehicle in which the grip surface and a rider's hand are exposed to outdoor environmental conditions. The system has an electrical power source; a resistive heating element mounted to the grip surface for warming the grip surface; an automatic temperature controller having a switch electrically connected in series between the power source and the heating element for switching power on and off to the heating element in response to a temperature feedback signal; and, a temperature sensor electrically connected to the temperature controller for providing the temperature feedback signal and mounted on the grip surface at an interface between the grip surface and the hand, the grip surface and the hand being exposed to outdoor environmental conditions. The system is particularly useful for vehicles such as snowmobiles, snow throwers, ATV's and motorcycles.

22 Claims, 4 Drawing Sheets

AUTOMATIC TEMPERATURE CONTROL SYSTEM AND METHOD

FIELD OF THE INVENTION

The present invention is directed to an automatic temperature control system and method, in particular, a system for automatically warming a grip surface of a vehicle in which the grip surface and a rider's hands are exposed to the elements.

BACKGROUND OF THE INVENTION

There is a burgeoning use of vehicles, particularly recreational vehicles, in which the rider as well as the grip surfaces, for example operator grip surfaces used to control operation of the vehicles, are exposed to the elements. Such vehicles include, for example, snowmobiles, snow throwers, all-terrain vehicles (ATV's), motorcycles, etc. Grip surfaces include, for example, sets of handlebars, hand grips, combinations of handlebars and hand grips, etc.

One problem with such a vehicle, particularly when the vehicle is used in cold weather, is that a rider's hands can get very cold during operation of the vehicle since both the hands and the grip surface are exposed to the elements. To mitigate against this problem, the vehicle may be manufactured having a heating element, for example a resistive heating element such as heater coils, embedded in or mounted on the grip surface to warm the grip surface and the hands during operation of the vehicle.

However, control of the heating element to provide maximum comfort and safety while reducing power consumption continues to be a problem in the art. For example, current hand grip heating systems for snowmobiles require constant adjustment of the temperature setting as environmental conditions change (e.g. wind chill factor, ambient air temperature, amount of sunlight, body temperature of the rider, etc.). Since environmental conditions can change quite rapidly, an operator must adjust the temperature setting often, leading to distractions as well as to inefficiencies in temperature control. Such distractions increase the likelihood of accidents as the operator is not looking where he or she is going while changing the temperature setting.

U.S. Pat. No. 2,662,961 issued Dec. 15, 1953 to Sargent disclosed a thermally regulated internally heated steering or control wheel. While Sargent mentions that the device may be used in vehicles in which the steering mechanism is partially or completely exposed to the elements, it is evident from his discussion and the figures that the device is mainly intended to be used with steering wheels enclosed in the cabin of a car and that there is no appreciation of the importance of thermostat location.

U.S. Pat. No. 5,757,165 issued May 26, 1998 to Minks describes a snowmobile handlebar heater control. The system disclosed by Minks monitors the load on the power supply and adjusts power to the heating element based on the total power being supplied. Such a system is primarily concerned with power management with the handlebar heaters being of lesser importance. Thus, the system described by Minks is designed to provide less power to the handlebar heaters when there is a greater power demand from other parts in the system. Furthermore, the thermistor measures ambient temperature rather than the temperature at the interface between the handle bars and the operator's hands. Thus, it can be seen that rider comfort and safety is of secondary importance.

Equipment having exposed rider grips, such as some equipment in the recreational vehicle industry, has become more hi-tech and rider comfort and safety have become increasingly important. There is a continuing need in the art to provide a safe, simple and effective method of controlling heating elements in the grip surfaces of vehicles to increase the comfort of a rider while reducing power consumption.

SUMMARY OF THE INVENTION

In the present specification, reference is made to a rider's hand. It is evident to one skilled in the art that another appendage, for example a foot, may be used to grip a grip surface. It will be understood by one skilled in the art that, herein, reference to a hand is intended to also encompass other appendages, wherever appropriate.

According to an aspect of the invention, there is provided a system for automatically warming a grip surface of a vehicle in which the grip surface and a rider's hand are exposed to the elements, the system comprising: an electrical power source; a resistive heating element mounted to the grip surface for warming the grip surface; an automatic temperature controller comprising a switching means electrically connected in series between the power source and the heating element for switching power on and off to the heating element in response to a temperature feedback signal; and, a temperature sensor electrically connected to the temperature controller for providing the temperature feedback signal and mounted on the grip surface at an interface between the grip surface and the hand, the grip surface and the hand being exposed to the elements.

According to another aspect of the invention, there is provided a method of controlling a heating element for a grip surface of a vehicle in which the grip surface and a rider's hand are exposed to the elements, the vehicle having an electrical power source for providing power to the heating element, the method comprising: measuring temperature in an interface between the grip surface and the hand, the grip surface and the hand being exposed to the elements; comparing the temperature to a set temperature; and, switching on the power to the heating element when the temperature is lower than the set temperature and switching off the power to the heating element when the temperature is higher than the set temperature.

The system and method of the present invention are primarily directed to enhancing the comfort and/or safety of a vehicle rider. It has been found that the location of the temperature sensor is important for effective control of temperature and for maximizing comfort level for the rider. The rider may be an operator of the vehicle, a passenger, or both. Automatic temperature control provided by the present invention further permits the operator of a vehicle to concentrate on operating the vehicle while remaining comfortable, thereby increasing safety since the operator does not have to manually adjust the temperature control with changing conditions in the surrounding environment to maintain a desired temperature.

In the present invention, the temperature sensor is mounted on the grip surface in a location where the sensor is able to monitor the temperature in an interface between the grip surface and the rider's hand. Prior art systems, for example those disclosed in U.S. Pat. No. 2,662,961 and U.S. Pat. No. 5,757,165, include thermistors which monitor ambient air temperature, rather than the temperature in the interface between the grip surface and the rider's hand. This requires the operator to increase the temperature setting above the desired interface temperature in order to attain the desired interface temperature. The present invention therefore leads to more accurate and effective temperature control as compared to the prior art, thereby increasing comfort and safety.

Prior art systems for controlling handlebar heaters have been expensive, relatively complicated and have afforded little control over temperature while consuming too much power. In contrast, the system of the present invention is relatively inexpensive, simple and provides good automatic control over the temperature of grip surfaces consuming only the power needed to maintain the desired temperature, which generally results in reduced power consumption as compared the prior art.

The present invention is useful in association with vehicles in which the rider's hand and the vehicle's grip surfaces are exposed to the elements. Some examples of such vehicles are snowmobiles, snow throwers, ATV's and motorcycles. Vehicles that are operated when the ambient air temperature is cold are of particular note.

The grip surface may be an operator grip surfaces or a passenger grip surface, and is any suitable means that permits a vehicle rider to hold on to while riding the vehicle. In the case of a snow thrower, the rider may not actually be riding on the vehicle, but may be walking behind it. For example, a grip surface may be a set of handlebars, a steering wheel, a joystick, control levers, etc. In many vehicles such as those described previously, an operator grip surface is usually a set of handlebars that may comprise hand grips for use with the operator's hands, and a passenger grip surface may be a hand grip.

The temperature sensor is located so that it has good thermal grip interface with the grip surface. The temperature sensor may be mounted on the grip surface under the hand of the rider. Thus, the temperature sensor is monitoring the temperature of the grip surface at the point where the hand makes contact with the grip surface. The temperature sensor is mounted in a location where good thermal grip interface is maintained at all times. Where the grip surface is a set of handlebars for an operator, the temperature sensor may be mounted on the handlebars where the operator's hand will be in contact with the handlebars. Thus the temperature sensor would be between the hand the handlebars, for example, under the palm, under the fingers or under both the palm and the fingers (e.g. at the joint between the palm and the fingers). Where hand grips are used, the temperature sensor may be mounted to a grip under where the fingers contacts the grip during normal operation of the vehicle. For snowmobiles, the temperature sensor is preferably located at the front of the grip under the fingers. The temperature sensor may be embedded within the grip or affixed to a surface of the grip.

If more than one hand is warmed, more than one temperature sensor may be used, although this is not necessary. Thus, there may be two, three or more temperature sensors electrically connected to a single controller. In another embodiment, the vehicle may be equipped with separate systems, one for each hand or one for each pair of hands. In one embodiment, there may be two temperature sensors each independently connected to separate controllers to provide independent temperature control for each hand.

In order to warm the grip surface and the rider's hand, any suitable resistive heating element may be used, for example resistance wires (e.g. heater coils), flexible sheet or flat heaters, etc. The heating element is mounted to the grip surface. The heating element may be mounted on or embedded in the grip surface. Where a hand grip is used, the heating element may be mounted on or embedded in the hand grips.

Any suitable temperature detector may be used, for example thermistors, thermocouples, bimetallic strips, resistance temperature detectors (RTD's), expansion chamber temperature sensors, etc. Thermistors are preferred as they respond quickly to changing conditions. The temperature detector provides a feedback signal to the automatic temperature controller to enable the switching means to turn power on or off to the heating element based on the temperature in the interface. In this way, the temperature in the interface may be controlled. Electronic components of the automatic temperature controller may be encased in a high density resinous material and/or a metal container to provide waterproofing.

The grip surface may be maintained at any desired temperature, the preferred temperature being dependent on a particular rider. In general, the heating element should be able to maintain the temperature of the grip surface in a range of from about 15° C. to about 35° C. Temperatures in a range of from about 18° C. to about 30° C. and from about 22° C. to about 28° C. are of particular note. The system may comprise an option for the rider to pre-select the desired temperature at any level within the range, thus, the system may have a variable pre-set temperature reference in the circuit against which the temperature as measured by the temperature sensor is compared. Once the rider finds a pre-selected temperature which is comfortable for that person, the pre-selected temperature need not, usually, be set again for that rider.

The system of the present invention automatically maintains the temperature of the grip surface at a pre-selected value (i.e. a pre-set temperature) by means of a feedback signal from the temperature sensor to the automatic temperature controller to form a closed loop. When the temperature falls below the pre-set temperature, the switching means of the automatic temperature controller switches power on to the heating element to warm the grip surface. When the temperature reaches the pre-set temperature, the switching means of the automatic temperature controller switches power off to the heating elements. While one pre-set temperature may trigger both the switching on and switching off of the power to the heating element, such an arrangement may lead to difficulties with rapid oscillation of the switching means. In order to mitigate against such oscillation, it is preferred to build hysteresis or dead band into the system by having a first set temperature below which the switching means will switch on the power to the heating element and a second set temperature above which the switching means will switch off the power to the heating element. The difference between the first and second set temperatures may be any desired value. A difference of about 0.5° C. to 3° C. may be particularly mentioned. A difference of about 1° C. to 2° C. may be more particularly mentioned. The first set temperature may be tied to the second set temperature, with the second set temperature being pre-selectable by the rider in a manner as described above. Thus, the first set temperature will be a fixed amount lower than the second set temperature but the actual value of the first set temperature will depend on the value of the second set temperature pre-selected by the rider.

Any suitable electrical power source may be used. The power source may be AC or DC and may be separate from or the same as the power source used to run other electrical components of the vehicle. An alternator of the vehicle is of particular note as a source of electrical power. The system may comprise a power indicator that indicates whether the power to the heating element is on or off. Any suitable indicator may be used, for example visual and/or auditory indicators. Since the operation of most vehicles would interfere with perception of an auditory indicator, a visual indicator is preferred. For example, an illuminated digital or analog meter, a light bulb, a light emitting diode (LED) or combinations thereof may be used.

The system of the present invention may be built into a vehicle during manufacturing of the vehicle, or it may be a so-called after-market system which is installed after the vehicle is manufactured.

When the system is built into the vehicle during manufacturing of the vehicle, it is advantageous to embed the temperature sensor within the grip surface near the surface of the grip surface. For example, for handlebars with hand grips, it is advantageous to embed the temperature sensor in the grip on the front of the grip near the surface of the grip where the operator's hand will cover the grip.

When the system is installed as an after-market product, it is desirable to ensure that the temperature sensor is affixed to a surface of the grip surface using a means that permits and maintains intimate contact of the temperature sensor with the grip surface. Such means may be, for example, elastic (e.g. rubber) bands, rubber or thermoplastic tape, etc.

Further features of the invention will be described or will become apparent in the course of the following detailed description.

BRIEF DESCRIPTION OF THE DRAWINGS

In order that the invention may be more clearly understood, a preferred embodiment thereof will now be described in detail by way of example, with reference to the accompanying drawings, in which.

DESCRIPTION OF PREFERRED EMBODIMENT

Figure 1:
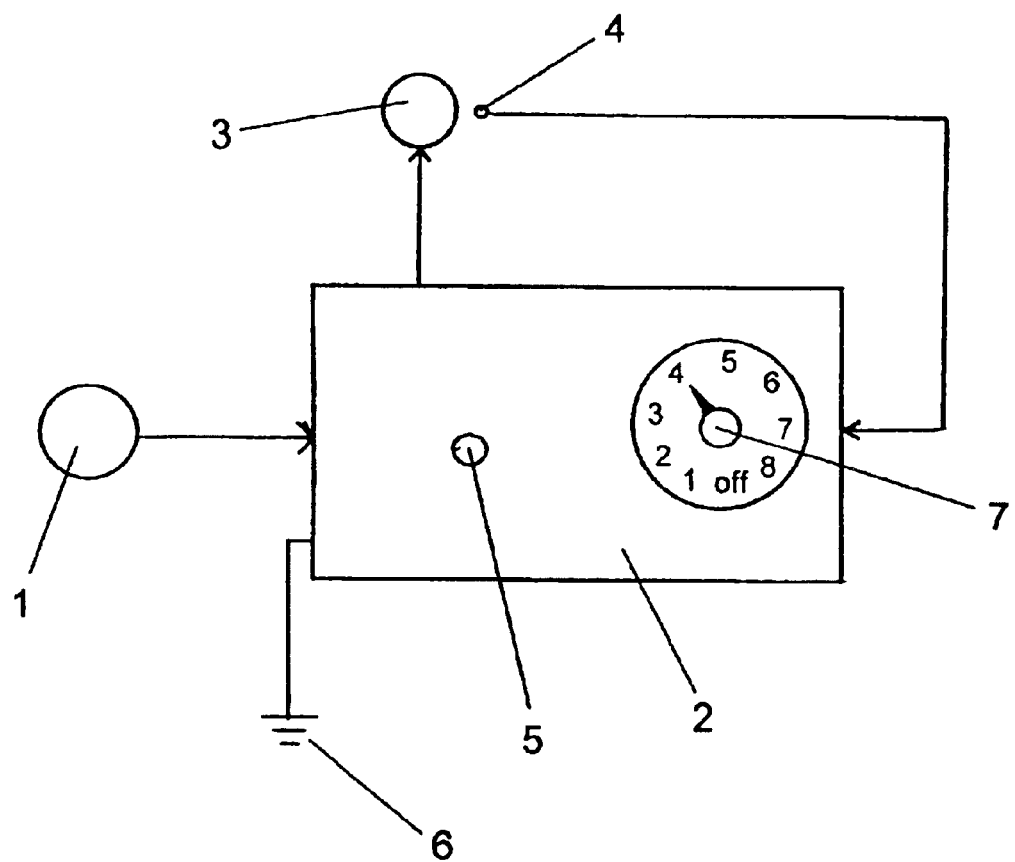
FIG. 1 is a pictorial representation of the system of the present invention.

FIG. 1 is a schematic diagram of the system of the present invention in which a source of 12 volt AC power such as an alternator (1) of a snowmobile (not shown) delivers power to heater coils (3) mounted in hand grips (not shown) of the snowmobile. Between the alternator (1) and the heater coils (3) is an automatic temperature controller comprising a switching means (2) which either switches on or switches off the power to the heater coils (3). A thermistor (4) is mounted in one of the hand grips near its surface where the fingers of an operator's hand contacts the hand grip. The thermistor (4) measures the temperature of the hand grip at the interface between the hand grip and the operator's hand. Feedback from the thermistor (4) to the automatic temperature controller (2) triggers an on or off response, either permitting or preventing power delivery from the alternator (1) to the heater coils (3) depending on the difference between the temperature as measured by the thermistor (4) and a set temperature as pre-set by the operator using a set point control knob (7). When the power is on, an LED indicator (5) is lit and when the power is off, the LED indicator (5) is unlit. The automatic temperature controller (2) is grounded to the snowmobile chassis by ground (6). However, one skilled in the art will recognize that the temperature controller (2) does not necessarily need to be grounded.

In FIG. 1, the set point control knob (7) has eight numbered settings, each numbered setting corresponding to a certain second set temperature. While the control knob (7) is depicted with eight numbered settings, the knob itself may be designed to turn in discrete steps from one numbered setting to another, or it may be designed to be totally variable between each numbered setting with the numbered settings simply functioning as a visual guide to an operator. The automatic temperature controller (2) also has a first set temperature for each second set temperature and tied to each second set temperature. The first set temperatures are 1° C. lower than the corresponding second set temperatures. There is also an 'off' setting if the operator does not wish to use the heater coils (3).

In operation, when the snowmobile operator requires the use of the heater coils (3), he or she turns the set point control knob (7) from 'off' to a desired setting, for example the setting '4' which corresponds to a specific second set temperature, for example 22° C. Since the ambient temperature is cold, for example –15° C., the hand grips will also be cold and the thermistor (4) initially measures a temperature of somewhat less than 22° C. The automatic temperature controller (2) receives this information from the thermistor (4) and compares the temperature at the thermistor (4) with the second set temperature, i.e. 22° C. Recognizing that the measured temperature is lower than the second set temperature, the automatic temperature controller (2) switches power on to the heater coils (3) and the LED indicator (5). The heater coils (3) remain on until the hand grip has warmed up to 22° C., at which time the automatic temperature controller (2), comparing the feedback from the thermistor (4) with the second set temperature, switches off the power to the heater coils (3) and the LED indicator (5). The hand grip then starts to cool down. When the temperature of the hand grip reaches a temperature corresponding to the first set temperature for that particular controller setting, the automatic temperature controller (2) switches on the power to the heater coils (3) thus beginning the warming cycle anew. Warming and cooling cycles are automatically repeated in this manner.

Figure 2:
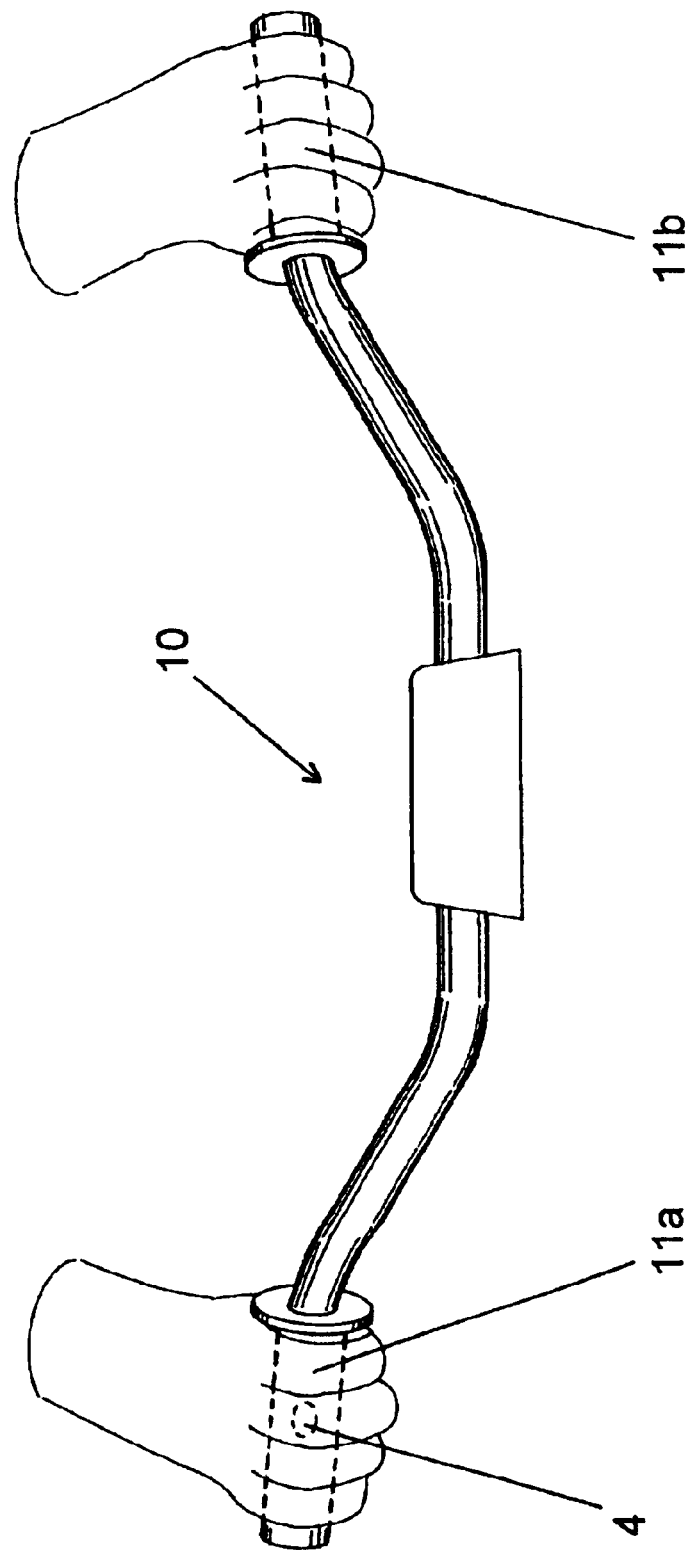
FIG. 2 is a pictorial representation of a front view of a set of handlebars of a snowmobile depicting the location of the thermistor of the system of FIG. 1 in relation to an operator's hand.

FIG. 2 provides a better indication of the location of the thermistor (4) on the hand grip (11a). In this embodiment, there are two hand grips (11a, 11b) mounted on a set of handlebars (10) of a snowmobile (not shown). Both hand grips (11a, 11b) have heater coils (not shown) embedded in them, but only one of the hand grips (11a) is equipped with a thermistor (4). Other embodiments may have a thermistor associated with each hand grip. It is evident from FIG. 2 that the thermistor (4) is located on the hand grip (11a) where the fingers of an operator's hand contact the hand grip (11a).

Figure 3:
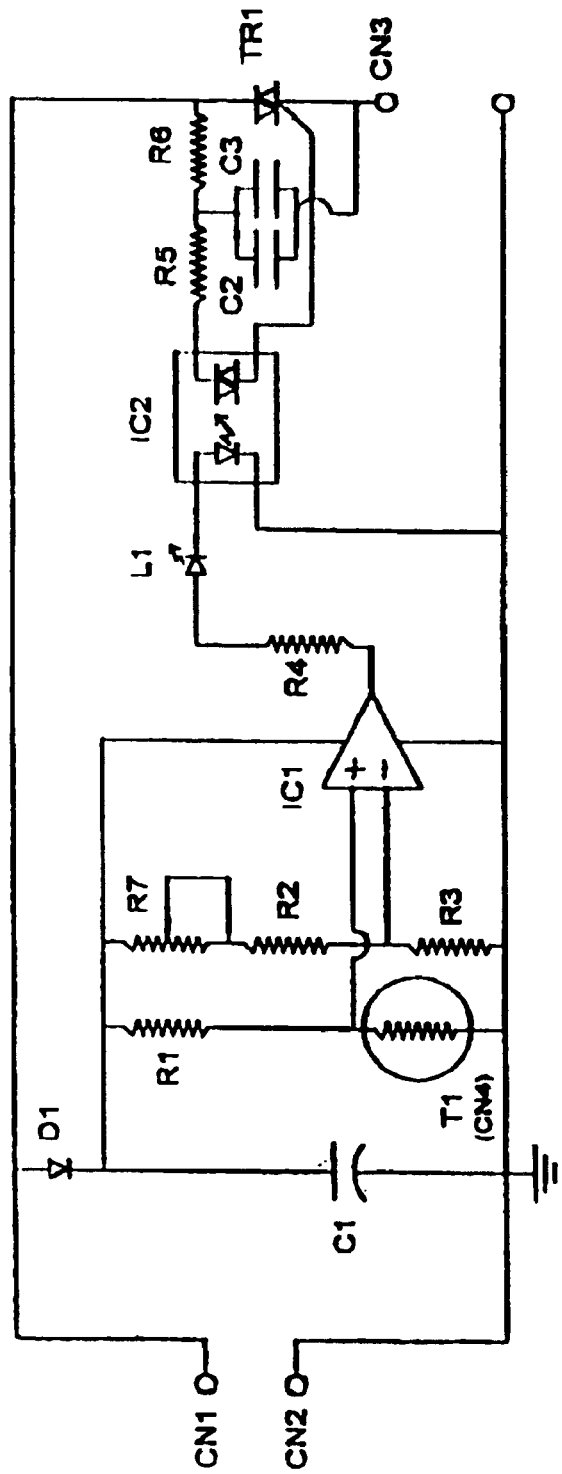
FIG. 3 is a circuit diagram of an embodiment of the system of the present invention; and, FIG. 4 is a graph of temperature (° C.) versus time (minutes) illustrating the ability of a system of the present invention to maintain the temperature of a grip surface at about 25° C. when the ambient temperature is –15.1° C.

FIG. 3 is a circuit diagram of an embodiment of the system of the present invention. The circuit comprises the components listed in Table 1. FIG. Ref. refers to the reference numerals in FIG. 3.

TABLE 1

| FIG. Ref. | Component | Manufacturer/Part No. |
|---|---|---|
| CN1 | ¼" spade connector, PCB mount | Keystone/1287 |
| CN2 | ¼" spade connector, PCB mount | Keystone/1287 |
| CN3 | ¼" spade connector, PCB mount | Keystone/1287 |
| D1 | rectifying diode | National/1N4002 |

TABLE 1-continued

| FIG. Ref. | Component | Manufacturer/Part No. |
|---|---|---|
| C1 | electrolytic capacitor, 100 µF, 25 V, radial mount | United Chemicon/ SME25VB101M6X1111 |
| R1 | resistor, 100 K ¼ watt | Phillips/CR25 |
| T1 | thermistor, 100 K nominal | Fenwall/140 104QAG-A01 |
| R2 | resistor, 82 K ¼ watt | Phillips/CR25 |
| R3 | resistor, 150 K ¼ watt | Phillips/CR25 |
| IC1 | dual OP amp, 8 pin dip | National/LM358 or LM2904M |
| R4 | resistor, 1 K ¼ watt | Phillips/CR25 |
| L1 | LED, red high intensity, T1 case | Liteon/LT216KE |
| IC2 | opto-coupler, DIAC output | Motorola/MOC301 |
| R5 | resistor, 100 ohm ¼ watt | Phillips/CR25 |
| R6 | resistor, 470 ohm ¼ watt | Phillips/CR25 |
| C2 | capacitor, 0.1 µF 50 V, film | Phillips/CZ20C104M |
| C3 | capacitor, 0.1 µF 50 V, film | Phillips/CZ20C104M |
| TR1 | TRIAC | Motorola/T2800D or 2N6071A |
| CN4 | locking header, 0.1" spacing, PCB mount | Panduit/MLSS100-2 |
| R7 | potentiometer, 100 K square body, PCB mount | Bourns/PCWIJ-B24-BAB104 |

Referring to FIG. 3, an automatic temperature controller for use on a snowmobile comprises connections, a rectifier, a comparator, an indicator, an isolator and a power control.

Connections: CN1 and CN2 are connection points for supplying the snowmobile's AC power to the circuit. CN3 is a connector for providing switched power to heater coils. CN4 is a plug for connecting the thermistor (T1) signal to the circuit.

Rectifier: Diode D1 and capacitor C1 form a simple half wave rectifier that is used to change the snowmobile's 12 volt AC power into DC, which is necessary to operate the comparator and isolator.

Comparator: The comparator is used to compare the pre-set temperature to the actual temperature and provide a control signal to the isolator and power control based on that comparison. The voltage at resistor R3 (negative input to OP amp IC1) is proportional to the set or desired temperature of the control surface and is selected by the operator when adjusting variable resistor R7. The voltage at thermistor T1 (positive input to OP amp IC1) is proportional to the actual temperature of the control surface as measured by the thermistor T1. The normal state of the circuit when the control surface is colder than the desired temperature is that the voltage at resistor R3 would be lower than the voltage at thermistor T1 causing a positive output from OP amp IC1. When the control surface reaches the desired temperature, the voltage at thermistor T1 falls below the voltage at resistor R3 causing the output of OP amp IC1 to go negative. Resistors R1 and R2 complete the comparator.

Indicator: When the output of OP amp IC1 is positive, current flows through resistor R4, LED L1 and the infrared LED inside opto-coupler IC2, thereby causing LED L1, to light indicating to the operator that power is being delivered to the heater coils. Resistor, R4, controls the brightness of LED L1.

Isolator: Opto-coupler IC2, is used to isolate the DC control signal provided by OP amp IC1 from the AC signal that powers the heater coils. When the output of OP amp IC1 is positive, current flows through resistor R4, LED L1 and the infrared LED inside opto-coupler IC2. Light emitted by the infrared LED inside opto-coupler IC2 turns "on" the DIAC inside opto-coupler IC2 and allows AC current to flow to the gate of TRIAC TR1 through resistors R5 and R6.

Power Control: Heater coils typically require relatively high current, 1 to 3 amps, to operate. Since the DIAC output of opto-coupler IC2 cannot handle such currents, a power switching device such as a TRIAC is needed to control the power delivered to the heater coils. When current is applied to the gate of TRIAC TR1, by the DIAC inside opto-coupler IC2, current flows through TRIAC TR1 and causes the heater coils to warm.

If the combination of opto-coupler IC2 and TRIAC TR1 was replaced by a power transistor, the circuit could be used on vehicles that use DC power. If the combination was replaced by a relay, then the same circuit could be used to control both AC and DC powered vehicles. Relays, however, are more expensive, noisy and do not have the same longevity as transistors or TRIACS.

Figure 4:
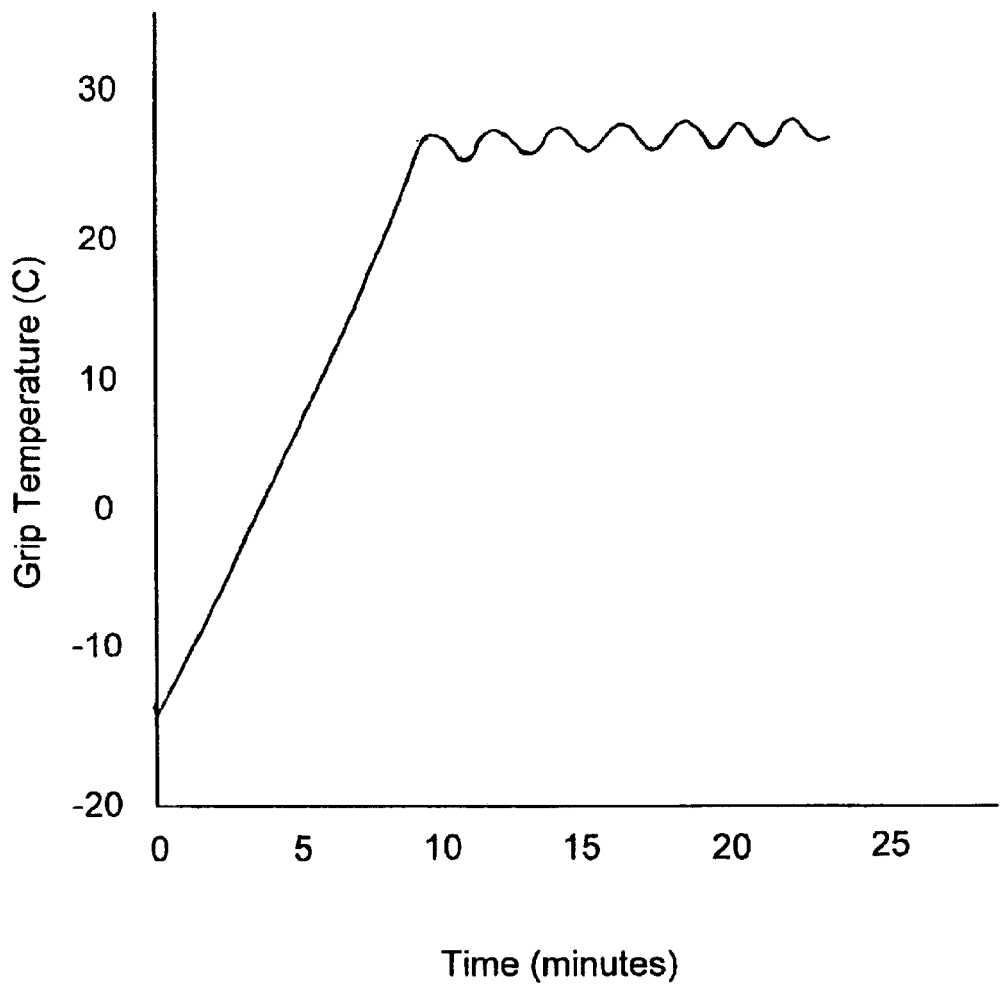

FIG. 4 is a graph of temperature (° C.) versus time (minutes) illustrating the ability of the circuit of FIG. 3 to maintain the temperature of a grip surface at about 25° C. when the ambient temperature is −15.1° C. It is evident from FIG. 4 that the temperature initially rises until a temperature of about 25.5° C. is reached at about the 10 minute mark. After that, the temperature oscillates regularly for another 13 minutes between a temperature of about 25.5° C. and 24.5° C. (a hysteresis of about 1° C) without any wild fluctuations or tapering off. This demonstrates the reliability and accuracy of the circuit.

Other advantages which are inherent to the structure are obvious to one skilled in the art.

It will be understood that certain features and sub-combinations are of utility and may be employed without reference to other features and sub-combinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having described the invention, what is claimed is:

1. A system for automatically warming a grip surface of a vehicle in which the grip surface and rider's hand are exposed to outdoor environmental conditions, the system comprising:
    (a) an electrical power source;
    (b) a resistive heating element mounted to the grip surface for warming the grip surface;
    (c) an automatic temperature controller comprising a switching means electrically connected in series between the power source and the heating element for switching power on and off to the heating element in response to a temperature feedback signal; and,
    (d) a temperature sensor electrically connected to the temperature controller for providing the temperature feedback signal and mounted on the grip surface at a location to measure temperature at an outer surface of the grip surface under a palm, fingers, or palm and fingers of the hand, the grip surface and the hand being exposed to the outdoor environmental conditions.

2. The system according to claim 1, wherein the temperature sensor is embedded within the grip surface proximal the outer surface.

3. The system according to claim 1, wherein the temperature sensor is affixed to the outer surface of the grip surface.

4. The system according to claim 3, wherein the temperature sensor is affixed to the outer surface of the grip surface with an elastic band or rubber or thermoplastic tape.

5. The system according to claim 1, wherein the grip surface comprises a set of handlebars.

6. The system according to claim 5, wherein the set of handlebars comprises a hand grip.

7. The system according to claim 6, wherein the temperature sensor is embedded within the hand grip proximal the outer surface of the hand grip.

8. The system according to claim 6, wherein the temperature sensor is affixed to the outer surface of the hand grip.

9. The system according to claim 1, wherein the vehicle is a snowmobile, a snow thrower, an ATV or a motorcycle.

10. The system according to claim 1, wherein the temperature sensor is a thermistor.

11. A method of controlling a heating element for a grip surface of a vehicle in which the grip surface and a rider's hand are exposed to outdoor environmental conditions, the vehicle having an electrical power source for providing power to the heating element, the method comprising:
 (a) measuring temperature at an outer surface of the grip surface under a palm, fingers, or palm and fingers of the hand, the grip surface and the hand being exposed to the outdoor environmental conditions;
 (b) comparing the temperature to set temperature: and,
 (c) switching on the power to the heating element when the temperature is lower than the set temperature and switching off the power to the heating element when the temperature is higher than the set temperature.

12. The method according to claim 11, wherein the set temperature comprises a first set temperature and a second set temperature, and wherein the power to the heating element is switched on when the temperature is lower than the first set temperature, and wherein the power to the heating element is switched off when the temperature is higher than the second set temperature.

13. The method according to claim 11, wherein the grip surface is a hand grip.

14. The method according to claim 12, wherein the grip surface is a hand grip.

15. The method according to claim 14, further comprising the step of selecting the second set temperature prior to measuring the temperature.

16. The method according to claim 15, wherein the second set temperature is selected to be in a range from 22° C. to 28° C.

17. A system for automatically warming a hand grip of a snowmobile comprising:
 (a) an electrical power source;
 (b) a heating element mounted to the hand grip;
 (c) an automatic temperature controller comprising a switching means electrically connected in series between the power source and the heating element for switching power on and off to the heating element in response to a temperature feedback signal; and,
 (d) a thermistor electrically connected to the temperature controller for providing the temperature feedback signal, the thermistor mounted on the hand grip at a location to measure temperature at an outer surface of the hand grip under a palm, fingers, or palm and fingers of an operator's hand, the hand grip and the hand being exposed to outdoor environmental conditions.

18. The system according to claim 17, wherein the thermistor is located at a front of the hand grip under the fingers.

19. The system according to claim 17, wherein the thermistor is embedded within the hand grip proximal the outer surface under the hand.

20. The system according to claim 17, wherein the thermistor is affixed to the outer surface of the hand grip under the hand.

21. The system according to claim 20, wherein the thermistor is affixed to the outer surface of the hand grip with an elastic band or rubber or thermoplastic tape.

22. The system according to claim 17, wherein the snowmobile has two hand grips and each hand grip has a said heating element mounted thereto for warming the hand grip.

* * * * *